US006448379B1

(12) United States Patent
Tekamp-Olson et al.

(10) Patent No.: US 6,448,379 B1
(45) Date of Patent: Sep. 10, 2002

(54) IL8 INHIBITORS

(75) Inventors: Patricia Tekamp-Olson, San Anselmo; Guy Mullenbach, San Francisco; Mary Ellen Wernette-Hammond, Leandro, all of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 08/121,105

(22) Filed: Sep. 14, 1993

(51) Int. Cl.$^7$ ........................ C07K 16/00; A61K 39/395
(52) U.S. Cl. ............................ 530/388.2; 530/388.22; 530/388.85; 424/139.1; 424/152.1
(58) Field of Search ..................... 435/240.27, 172.2, 435/70.21, 326; 530/388.22, 388.2, 388.85; 424/139.1, 152.1

(56) References Cited

U.S. PATENT DOCUMENTS

| | | | |
|---|---|---|---|
| 5,374,506 A | * | 12/1994 | Murphy |
| 5,440,021 A | * | 8/1995 | Chuntharapai et al. |
| 5,552,284 A | * | 9/1996 | Lee et al. |
| 5,595,915 A | * | 1/1997 | Geysen |

FOREIGN PATENT DOCUMENTS

| | | | |
|---|---|---|---|
| EP | 0 480 381 | | 4/1992 |
| WO | WO92/04372 | | 3/1992 |
| WO | 9218641 | * | 10/1992 |
| WO | WO93/06229 | | 4/1993 |

OTHER PUBLICATIONS

Lerner et al Nature vol. 299: 592–596, 1982.*
marglin et al Ann Rev Biochemistry vol. 39: 841–866, 1970.*
Galfre et al Methods in Enzymology vol. 73 1–46, 1981.*
Harlow et al. Antibodies A Laboratory Manual, CSHL Press 1988, pp. 285–287.*
Harris et al. TIBTECHII:42–44, 1993.*
Baggiolini et al., Interleukin–8, a chemotactic and inflammatory cytokine, (1992) *Fed. of Euro. Biochem. Soc.*, 307:97–101.
Bazzoni, F. et al., Phagocytosing neutrophils produce and release high amounts of the neutrophil–activating peptide 1/interleukin, (1991) *J. Exp. Med.* 173:771–774.
Gayle et al., Importance of the *amino terminus* of the Interleukin–8 receptor in ligand interactions, *J. Biol. Chem.* (1993) 268:7283–7289.
Geiser et al., The interleukin–8–related chemotactic cytokines GROα, GROβ, and GROγ activate human neutrophil and basophil leukocytes, *J. Biol. Chem.* (1992) 206:15419–15324.
Holmes et al., Structure and functional expression of a human interleukin–8 receptor *Science* (1991) 253:1278–1280.

LaRosa et al., *Amino terminus* of the Interleukin–8 receptor is a major determinant of receptor subtype specificity, *J. Biol. Chem.* (1992) 267:25402–25406.
Larson, C.G. et al., The neutrophil–activating protein (NAP–1) is also chemotactic for T lymphocytes, (1989) *Science* 243:1464–1466.
Lewis, M., et al., Cloning and expression of cDNAs for two distinct murine tumor necrosis factor receptors demonstrate one receptor is species specific, (1991), *Proc. Natl. Acad. Sci USA*, 88:2830–2834.
Matsushima, K. et al., Molecular cloning of a human monocyte–derived neutrophil chemotactic factor (MDNCF) and the induction of MDNCF mRNA by interleukin 1 and tumor necrosis factor, (1988) *J. Exp. Med.* 167:1883–1893.
Moser, B. et al., Neutrophil–activating peptide 2 and gro/melanoma growth–stimulatory activity interact with neutrophil–activating peptide 1/interleukin 8 receptors on human neutrophils, (1991) *J. Biol. Chem.* 266:10666–10671.
Mukaida, N. et al., Genomic structure of the human monocyte–derived neutrophil chemotactic factor IL–8, (1989) *J. Immunol.* 143:1366–1371.
Ribeiro, R.A. et al., IL–8 causes in vivo neutrophilmigration by a cell–dependent mechanism, (1991) *Immunology* 73:472–477.
Schröder, J.M. et al., Purification and partial biochemical characterization of a human monocyte–derived, neutrophil–activating peptide that lacks interleukin 1 activity, (1987) *J. Immunol.* 139:3474–3483.
Schröder, J.M. et al., Purification and partial biologic characterization of a human lymphocyte–derived peptide with potent neutrophil–stimulating activity (1988) *J. Immunol.* 140:3534–3540.
Schröder, J.M., The monocyte–derived neutrophil activating peptide (NAP/Interleukin 8) stimulates human neutrophil arachidonate–5–lipoxygenase, but not the release of cellular arachidonate, (1989) *J. Exp. Med.* 170:847–861.
Suzuki, K. et al., Purification and partial primary sequence of a chemotactic protein for polymorphonuclear leukocytes derived from human lung giant cell carcinoma LU65C cells, (1989) *J. Exp. Med.* 169:1895–1901.
Van Damme, J. et al., A novel, $NH_2$–terminal sequence–characterized human monokine possessing neutrophil chemotactic, skin–reactive, and granulocytosis–promoting activity, (1988) *J. Exp. Med.* 167:1364–1376; and
Walz A., et al., Structure and neutrophil–activating properties of a novel inflammatory peptide (ENA–78) with homology to interleukin 8, (1991) *J. Exp. Med.* 174:1355–1362.

* cited by examiner

*Primary Examiner*—Mark Navarro
(74) *Attorney, Agent, or Firm*—Jane E. R. Potter; Kimberlin L. Morley; Robert P. Blackburn

(57) ABSTRACT

Inhibitors, including antibodies, of IL8 binding to its receptors, that interact with the amino-terminal extracellular domain of the IL8 receptor and which compete with IL8 for receptor-binding, are disclosed. The inhibitors are useful modulators of IL8 receptor-mediated biological activity.

4 Claims, 7 Drawing Sheets

```
                         #3
         #1
IL8R1   MSNITDPQMWDFDDLNFTGMPPADEDYSPCMLETETLNK

#12
            #11
     #10              #7
     #6                   #13
IL8R2   MESDSFEDFWKGEDLSNYSYSSTLPPFLLDAAPCEPESLEINK
```

*Fig. 1*

IL8 INHIBITORS

TECHNICAL FIELD

The present invention relates generally to cytokine inhibitors. More particularly, the invention relates to inhibitors to IL8 receptor binding, including antibodies, that interact with the amino-terminal extracellular domain of the IL8 receptor and compete with IL8 and other related natural ligands, for receptor-binding.

BACKGROUND OF THE INVENTION

Cytokines are a group of hormone-like mediators produced by leukocytes. These agents serve as endogenous biological signals that act in conjunction with antigens to amplify both localized and systemic host defense mechanisms involving macrophages, lymphocytes, and other cell types. Representative cytokines include the various interleukins, interferons, GROα, GROβ and GROγ, neutrophil activating peptide-2 (NAP-2) and ENA-78. Cytokines have been used to treat and prevent a wide variety of disorders based on the ability of these molecules to stimulate an immunological response.

Interleukin-8 (IL8) is a cytokine originally derived from human macrophages (Suzuki, K. et al. (1989) *J. Exp. Med.* 169:1895–1901; Schröder, J. M. et al. (1987) *J. Immunol.* 139:3474–3483; Schröder, J. M. et al. (1988) *J. Immunol.* 140:3534–3540; Schröder, J. M. (1989) *J. Exp. Med.* 170:847–861; Larson, C. G. et al. (1989) *Science* 243:1464–1466). This factor has also been called polymorphonuclear (PMN) chemotactic factor, monocyte-derived neutrophil-activating peptide (MONAP), monocyte-derived neutrophil chemotactic factor (MDNCF), T lymphocyte chemotactic factor (TCF), lymphocyte-derived neutrophil-activating peptide (LYNAP), and neutrophil-activating peptide 1 (NAP-1).

The IL8 molecule is produced by a wide variety of tissues and cells, including mononuclear phagocytes, endothelial cells, fibroblasts, epithelial cells and alveolar macrophages, upon stimulation with such agents as lipopolysaccharide and phorbol myristate, phytohemagglutinin, Con A, or other mitogenic preparations and cytokines such as interleukin-1 (IL1) and tumor necrosis factor (TNF). The gene coding for human IL8 has been cloned. Matsushima, K. et al. *J. Exp. Med.* (1988) 167:1883–1893; Mukaida, N. et al. *J. Immunol.* (1989) 143:1366–1371. The gene encodes a precursor protein having 99 amino acids which is proteolytically cleaved into secreted IL8 polypeptides of various lengths, such as those containing 69, 72 or 77 amino acid residues, with molecular masses of approximately 8000 Daltons.

Human IL8 acts as a chemoattractant for neutrophils, and induces granulocytosis upon systemic injection and skin reaction upon local injection, in experimental animals. Bazzoni, F. et al. (1991) 173:771–774; Van Damme, J. et al. (1988) *J. Exp. Med.* 167:1364–1376; Ribeiro, R. A. et al. (1991) Immunology 73:472–477. The molecule also activates the release of superoxide anions and elicits release of the primary granule constituents of neutrophils, including myeloperoxidase, β-glucuronidase and elastase. IL8 mediates these activities by binding to its receptor and triggering signal transduction, a cascade of reactions ultimately resulting in a biological response.

The sequences of two human IL8 receptors (termed "IL8R1" and "IL8R2" herein), have been reported. See, e.g., International Publication No. WO93/06229 (published Apr. 1, 1993) and Holmes et al. *Science* (1991) 253:1278–1280. These receptors have a similar affinity for IL8 and are members of the rhodopsin seven-helix membrane-spanning superfamily. These receptor molecules include seven transmembrane regions, linked by three intracellular and three extracellular loops and possess an extracellular amino-terminal tail and an intracellular carboxy-terminal tail. Other naturally occurring cytokines are known to share a receptor with IL8. For example, GROα, GROβ, GROγ, NAP-2 and ENA-78, all bind to one IL8 receptor on human neutrophils, as described in Baggiolini et al., *FEBS Lett.* (1992) 307:97–101; Walz et al., *J. Exp. Med.* (1991) 174:1355; Moser et al., *J. Biol. Chem.* (1991) 266:10666; Geiser et al., *J. Biol. Chem.* (1993) 268:15419–15424.

Gayle et al., *J. Biol. Chem.* (1993) 268:7283–7289 and LaRosa et al., *J. Biol. Chem.* (1992) 267:25402–25406 relate to an important determinant for the binding of natural IL8R2 agonists, GROα/MGSA and NAP-2, resides in the region of the receptor that includes the amino-terminal extracellular domain and a portion of the first transmembrahe region.

Peptides based on the sequence of the IL8 receptor have been constructed in an effort to determine the role of the various regions of the IL8 receptor in IL8 binding. Gayle et al., *J. Biol. Chem.* (1993) 268:7283–7289 describes peptides based on the amino-terminal sequence of the IL8 receptor and International Publication No. WO92/04372 (published Mar. 19, 1992) describes peptides and antibodies thereto based on the carboxy terminus of the receptor.

SUMMARY OF THE INVENTION

The present invention provides for substances that inhibit IL8 binding to its receptor via interaction with the amino-terminal extracellular domain of the IL8 receptor. The inhibitors are useful modulators of IL8 receptor-mediated biological activity.

Accordingly, in one embodiment, the invention is directed to an inhibitor to IL8 receptor-binding, as defined below, that comprises a molecule that is capable of interacting with the amino-terminal extracellular domain of an IL8 receptor and that is capable of competing with IL8 for the receptor.

In a preferred embodiment, the inhibitor is an antibody raised against a polypeptide derived from the amino-terminal extracellular domain of IL8R1 or IL8R2 comprising an amino acid sequence substantially the same as any one of the amino acid sequences M-S-N-I-T-D-P-Q-M-W-D-F-D-D-L, (SEQ ID NO:1) M-E-S-D-S-F-E-D-F-W-K-G-E-D-L, (SEQ ID NO:2) F-E-D-F-W-K-G-E-D-L-S-N-Y-S-Y, S-S-T-L-P-P-F-L-L-D-A-A-P-C (SEQ ID NO:3) or F-L-L-D-A-A-P-C-E-P-E-S-L-E-I (SEQ ID NO:5).

In another preferred embodiment, the invention includes a mixture of antibodies raised against at least four polypeptides derived from the amino-terminal extracellular domain of IL8R2, wherein
  (i) the amino acid sequence of the first polypeptide comprises an amino acid sequence substantially the same as the amino acid sequence M-E-S-D-S-F-E-D-F-W-K-G-E-D-I (SEQ ID NO:2);
  (ii) the amino acid sequence of the second polypeptide comprises an amino acid sequence substantially the same as the amino acid sequence F-E-D-F-W-K-G-E-D-L-S-N-Y-S-Y (SEQ ID NO:3);
  (iii) the amino acid sequence of the third polypeptide comprises an amino acid sequence substantially the same as the amino acid sequence S-S-T-L-P-P-F-L-L-D-A-A-P-C (SEQ ID NO:4); and
  (iv) the amino acid sequence of the fourth polypeptide comprises an amino acid sequence substantially the same as the amino acid sequence F-L-L-D-A-A-P-C-E-P-E-S-L-E-I (SEQ ID NO:5).

In another embodiment, the invention is directed to a method of inhibiting the binding of IL8 to its receptor, comprising:
(a) providing an inhibitor to IL8 receptor binding that is capable of binding to the amino-terminal extracellular domain of an IL8 receptor and is also capable of competing with IL8 for the receptor; and
(b) contacting the receptor with an effective inhibiting amount of the inhibitor.

In yet another embodiment, the invention is directed to a method of modulating an IL8 receptor-mediated biological response comprising:
(a) providing an inhibitor to IL8 receptor binding that is capable of binding to the amino-terminal extracellular domain of an IL8 receptor and that is capable of competing with IL8 for the receptor; and
(b) contacting a cell that produces an IL8 receptor with an effective modulating amount of the inhibitor.

In another embodiment, the invention is directed to an inhibitor to IL8 receptor-binding comprising a molecule that is capable of interacting with the amino-terminal extracellular domain of an IL8 receptor and that is capable of competing with a molecule selected from the group consisting of IL8, GROα, GROβ, GROγ, NAP-2 and ENA-78, for the receptor.

These and other embodiments of the subject invention will readily occur to those of ordinary skill in the art in view of the disclosure herein.

BRIEF DESCRIPTION OF THE FIGURES

FIG. 1 shows the amino acid sequences of the amino-terminal extracellular domain of human IL8R1 and human IL8R2 and depicts the peptides used to raise antisera.

DETAILED DESCRIPTION OF THE INVENTION

Figure 2A:
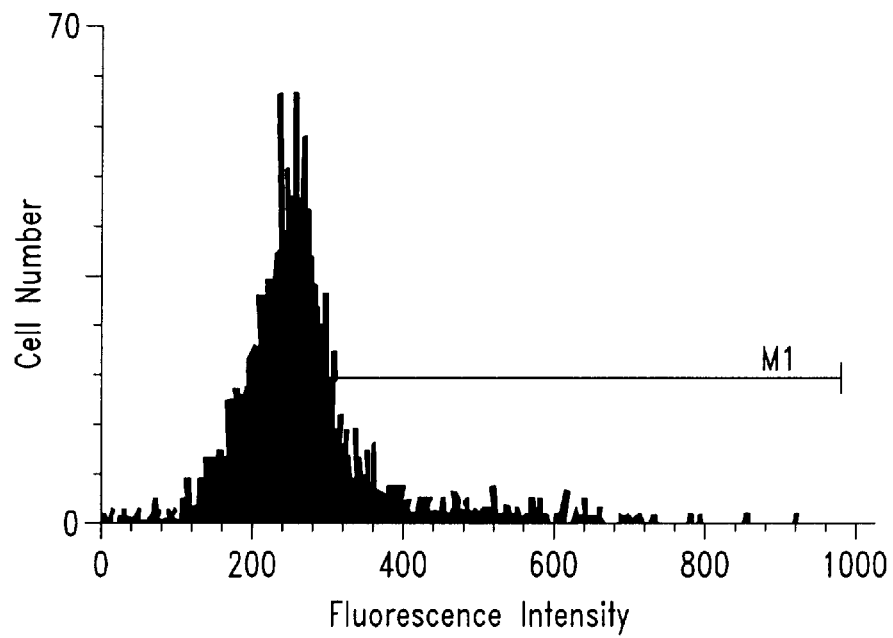
FIG. 2 shows the results of a FACS analysis of neutrophils using antisera to amino-terminal IL8R1 and IL8R2 peptides, as described in the examples. Neutrophils were incubated with sheep pre-immune IgG (FIGS. 2A and 2C), anti-IL8R1 peptide IgG (FIG. 2B) or anti-IL8R2 peptide IgG (FIG. 2D), each diluted 1:150 in PBS+1% BSA, then treated with fluoresein-labelled rabbit anti-sheep antibodies (1:100 in PBS+1% BSA) and subjected to FACS analysis, as described below.
Figure 2B:
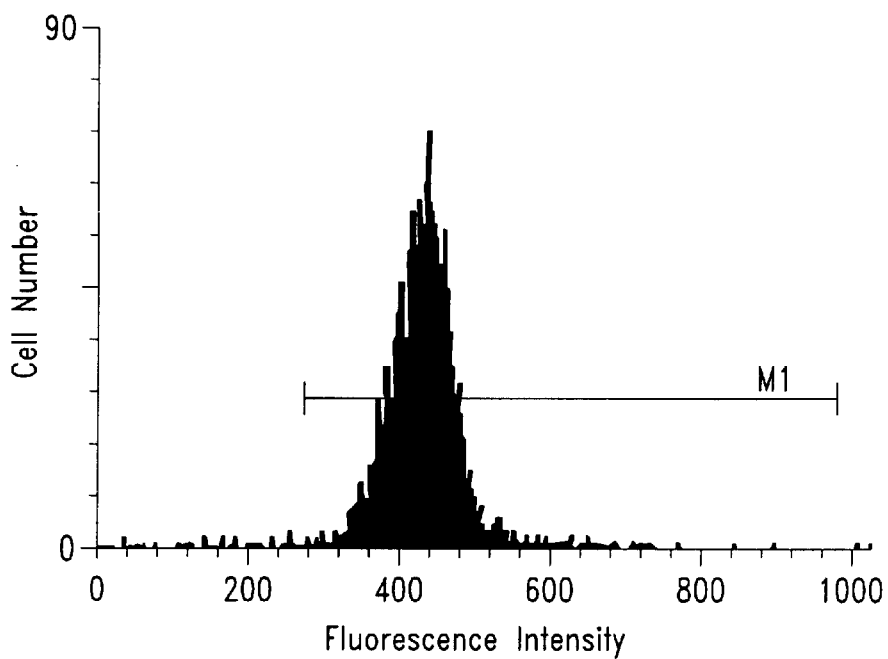
Figure 2C:
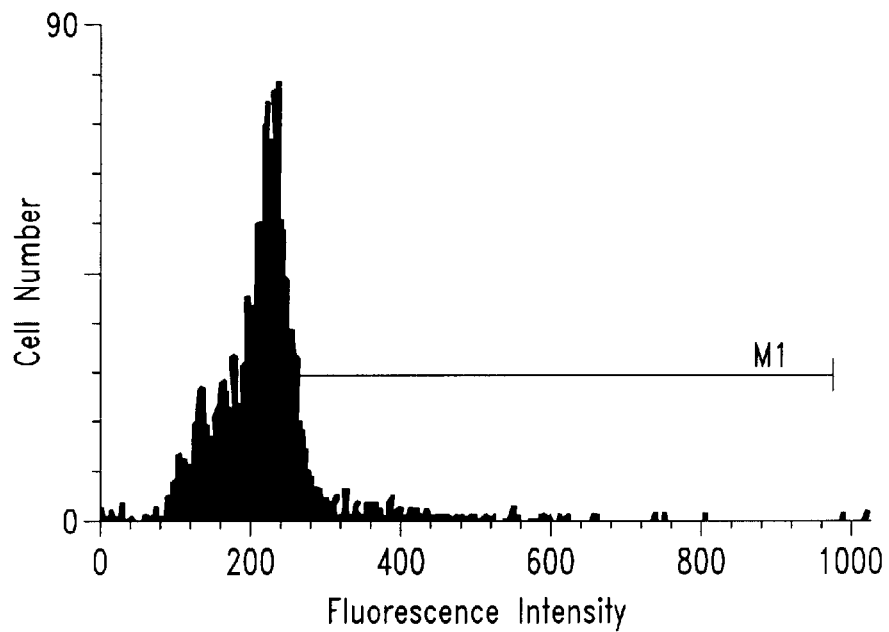
Figure 2D:
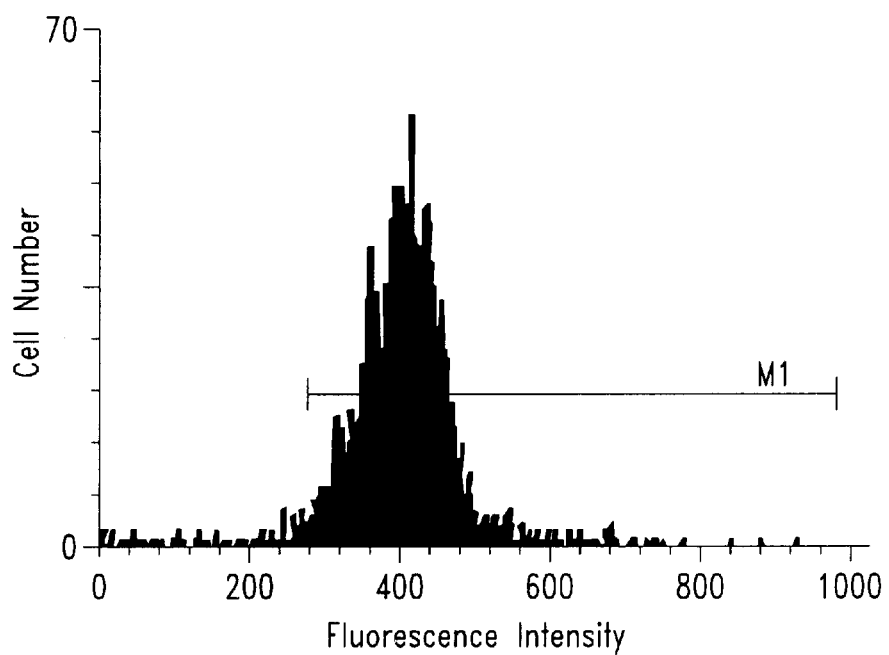

The practice of the present invention will employ, unless otherwise indicated, conventional methods of virology, microbiology, molecular biology and recombinant DNA techniques within the skill of the art. Such techniques are explained fully in the literature.

See, e.g., Sambrook, et al. *Molecular Cloning: A Laboratory Manual* (2nd Edition, 1989); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

An "inhibitor to IL8 receptor-binding" is a substance (other than native IL8 or other naturally occurring, endogenous neutrophil IL8 receptor ligands, such as GROα, β, γ, NAP-2, and ENA-78) which interacts either directly or indirectly with an IL8 receptor and competes with IL8 or other natural ligands, such as GROα, β, γ, NAP-2, and ENA-78, for binding to the receptor. IL8 receptor-binding interaction includes both covalent and non-covalent associations between the inhibitor and the IL8 receptor. Thus, the inhibitor can bind the IL8 receptor at an IL8 binding site in the amino-terminal extracellular domain and block IL8 binding. Alternatively, the inhibitor can interact with the IL8 receptor at a site other than the binding site and cause a conformational change in the receptor molecule that affects IL8 binding. Similarly, the inhibitor can interact with IL8 directly, either at the receptor-binding site or at another part of the molecule, and inhibit binding of IL8 to the receptor. Other possible interactions between the inhibitor, receptor and/or IL8 will readily occur to one of skill in the art and are also encompassed by this definition.

The ability of a molecule to bind an IL8 receptor and to compete with IL8 for receptor binding can be determined using conventional receptor-binding assays. For example, the ability of the inhibitor to bind the receptor can be assessed directly by labelling the inhibitor and demonstrating binding to receptor-bearing cells, such as neutrophils. Inhibitor binding can also be demonstrated by methods such as chemical cross-linking, by anti-inhibitor antibody recognition of the presence of the inhibitor bound to receptor-bearing cells, as described in the examples, by NMR or X-ray crystallography of inhibitor/receptor complexes, and/or by any other methods appropriate for use with a given inhibitor, generally known by a skilled practitioner. The ability of the inhibitors of the present invention to compete with IL8 for receptor binding can be determined using standard competition assays, such as the radioimmunoassays described in Gayle et al., *J. Biol. Chem.* (1993) 268:7283–7289; and LaRosa et al., *J. Biol. Chem.* (1992) 267:25402–25406 and in the examples herein. The molecule need not completely inhibit IL8 binding, but need only reduce the amount of binding that would normally occur in the absence of the inhibitor. Furthermore, an inhibitor of IL8 binding can be either an agonist, i.e., a molecule capable of promoting at least one of the biological responses normally associated with IL8, or an antagonist, i.e., a substance that opposes at least one of the effects of IL8, thereby reducing the ability of IL8 to mediate biological responses normally associated therewith.

The term "IL8 receptor," as used herein refers to any of the several vertebrate IL8 receptors, or fragments thereof which include an IL8 binding domain. For example, both human IL8R1 and IL8R2 are encompassed by this term.

The term "IL8 receptor-binding" or "IL8 binding" refers to the binding to any one of the IL8 receptors of any of IL8, GROα, GROβ, GROγ, NAP-2 and ENA-78, fragments thereof and other naturally occurring ligands.

By "modulating an IL8 receptor-mediated biological response" is meant either increasing or decreasing the incidence of one or more cellular activities normally triggered by the binding of IL8 to its receptor. The nature of these activities may be biochemical or biophysical. For example, a substance would "modulate an IL8 receptor-mediated biological response" if it does not stimulate the same signal transduction activity as IL8 when the inhibitor binds to an IL8 receptor. The increase or decrease can be monitored using various assays, described further below, which also utilize IL8 receptor molecules as controls.

More particularly, a cascade of biochemical reactions is triggered when IL8 binds to its receptor. Accordingly, an IL8 inhibitor will "modulate an IL8 receptor-mediated response" when it causes an increase or decrease in any one of these reactions. For example, IL8 receptors are G-coupled proteins which, when proper signal transduction activity occurs, triggers an increase of intracellular $Ca^{2+}$, $IP_3$, and DAG levels. Standard assays can be used to measure the intracellular levels of these substances and hence determine whether the IL8 receptor-mediated response has been modulated. Assays for measuring levels of free cytosolic $Ca^{2+}$ are known and described in, e.g., International Publication No. WO93/06229 (published Apr. 1, 1993); Bazzoni, F. et al. (1991) *J. Exp. Med.* 173:771–774 and Peveri, P. et al. (1988) *J. Exp. Med.* 167:1547–1559. Intracellular IP3 concentrations and DAG levels can also be measured by known methods.

Other biological activities attributable to IL8 which can be measured in order to determine modulation include, for example, neutrophil chemotactic activity, measured using assays generally known in the art (see, e.g., Schröder, J. M. et al. (1987) *J. Immunol.* 139:3474–3483; Fincham, N. J. et al. (1988) *J. Immunol.* 140:4294–4299; Larson, C. G. et al. (1989) *Science* 243:1464–1466; Grob, P. M. et al. (1990) *J. Biol. Chem.* 265:8311–8316; Strieter, R. M. et al. (1989) *J. Biol. Chem.* 264:10621–10626); enzyme release assays, such as PMN peroxidase-releasing activity assays, β-glucoronidase release assays, $O_2$-release as determined by cytochrome C assays and elastase release assays (see, e.g., Schröder, J. M. et al. (1987) *J. Immunol.* 139:3474–3483; Peveri, P. et al. (1988) *J. Exp. Med.* 167:1547–1559).

Two peptides will be "substantially the same" or "substantially identical" when at least about 50%, usually at least about 60%, more typically at least about 75% and preferably at least about 90–95%, of the amino acids match over a defined length of the molecule. As used herein, "substantially the same" also refers to sequences showing identity to the specified polypeptide sequence.

By "native IL8" is meant a polypeptide having an amino acid sequence which is identical to a sequence recovered from a source which naturally produces IL8. Native IL8 may be of varying lengths, such as those containing 69, 72 and 77 amino acid residues, respectively.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like.

The term "antibody" encompasses polyclonal and monoclonal antibody preparations, as well as preparations including hybrid antibodies, altered antibodies, $F(ab')_2$ fragments, F(ab) fragments, $F_v$ fragments, single domain antibodies, chimeric antibodies, humanized antibodies, and functional fragments thereof, which retain specificity for amino-terminal extracellular domain IL8 binding sites. For example, an antibody can include variable regions, or fragments of variable regions, which retain specificity for the amino-terminal extracellular domain of an IL8 receptor molecule. The remainder of the antibody can be derived from the species in which the antibody will be used. Thus, if the antibody is to be used in a human, the antibody can be "humanized" in order to reduce immunogenicity yet retain activity. For a description of chimeric antibodies, see, e.g., Winter, G. and Milstein, C. (1991) *Nature* 349:293–299; Jones, P. T. et al. (1986) *Nature* 321:522–525; Riechmann, L. et al. (1988) 332:323–327; and Carter, P. et al. (1992) *Proc. Natl. Acad. Sci. USA* 89:4285–4289. Such chimeric antibodies may contain not only combining sites for the IL8 receptor, but also binding sites for other proteins. In this way, bifunctional reagents can be generated with targeted specificity to both external and internal antigens.

An "antigen" or "immunogen" refers to a molecule which contains one or more epitopes that will stimulate a host's immune system to make a secretory, humoral and/or cellular antigen-specific response.

An "effective inhibiting amount" of an IL8 inhibitor refers to an amount of inhibitor sufficient to block the binding, in whole or part, of IL8 to the IL8 receptor. The precise effective inhibiting amount will depend upon the number and type of IL8 receptors present on the surface of the particular cell in question. Such an amount can be readily determined by one of skill in the art using routine experimentation and IL8 binding assays, such as standard neutrophil binding assays, as described in the examples.

The term "effective modulating amount" of an IL8 inhibitor refers to an amount of inhibitor sufficient to cause a change in an IL8 receptor-mediated biological activity, as described above. This amount will also depend on the number and type of IL8 receptors present on the surface of the particular cell in question and will vary depending on the biological activity targeted. Assays for determining changes in IL8 receptor-mediated activity are described above.

B. General Methods

Central to the present invention is the discovery of IL8 inhibitors that are capable of suppressing the binding of various ligands, including IL8, GROα, GROβ, GROγ, NAP-2 and ENA-78, to IL8 receptors, thereby modulating the biological responses triggered by such binding. Accordingly, these inhibitors can block or modulate chemotaxis and neutrophil activation. The inhibitors are useful for the treatment and prevention of a wide variety of disorders where neutrophils contribute to the pathology of the disease, including inflammatory diseases such as rheumatoid arthritis and inflammatory bowel disease, as well as for the treatment and/or prevention of tissue injury during such diseases as septic shock and acute respiratory distress syndrome (ARDS). The inhibitors of the present invention will also find use for stimulating neutrophil-mediated inflammatory response in the treatment of cancerous conditions, viral, bacterial, fungal and protozoal infections, as well as for the treatment of conditions where the immune system is compromised, such as AIDS and other acquired and inherited immune disorders.

The inhibitors of the present invention act at the amino-terminal extracellular domain of the IL8 receptor and include, for example, anti-amino-terminal extracellular domain antibodies, peptides, non-peptide small molecule inhibitors or any molecule that modulates IL8 action through interaction with the amino-terminal extracellular domain of the IL8 receptor.

The sequences of the amino-terminal extracellular domain of the human IL8 receptors 1 and 2 (termed IL8R1 and IL8R2, respectively) are shown in FIGS. 1 and 2. Inhibitors for use in the present invention include antibodies raised against isolated peptide sequences derived from contiguous sequences spanning this region, as well as antibodies raised against analogs thereof (i.e., sequences with amino acid substitutions, additions or deletions), which retain the ability to bind the IL8 receptor and inhibit the binding of IL8 thereto, as defined above. Surprisingly, it has been discovered that antibodies and mixtures of antibodies, generated to peptides derived from the amino-terminal extracellular domain region of both IL8R1 and IL8R2, are able to block the binding of IL8 to the receptor. Thus, the recognition site (epitope) for these antibodies appears to overlap with, or be proximal to, the IL8 recognition site. These antibodies can be polyclonal, monoclonal, chimeric, or functional fragments thereof, generated using standard techniques.

Furthermore, useful antibody preparations can include mixtures of several different antibodies, as detailed further below.

Peptides useful for raising antibody inhibitors will usually by at least about 5 amino acids in length, preferably 7–10 amino acids in length, and most preferably at least about 10 to 15 amino acids in length. There is no critical upper limit to the length of the fragment, which could comprise nearly the entire extracellular domain sequence, or even a fusion protein comprising fragments of two or more peptides from this region or one or more of the peptides fused to another protein sequence.

In particular, a number of peptides have been synthesized based on the amino acid sequence of the amino-terminal extracellular binding domain of IL8R1 and IL8R2. These peptides are shown in Tables 1 and 2, in the examples. These and other peptides may be synthesized by protein synthesis techniques known to those of skill in the peptide art. In general, these methods employ either solid or solution phase synthesis methods, well known in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

The peptides can also be produced by recombinant techniques, known in the art. For example, a DNA sequence encoding the peptide in question can be synthesized using standard methods. See, e.g., Edge (1981) *Nature* 292:756; Nambair et al. (1984) *Science* 223:1299; Jay et al. (1984) *J. Biol. Chem.* 259:6311. In general, one will select preferred codons for the intended host in which the sequence will be expressed. Alternatively, the sequence can be derived from genomic or cDNA. The DNA is cloned into an appropriate expression vector, either procaryotic or eucaryotic, using conventional methods, host cells transformed therewith and cultured under conditions allowing for expression of the protein of interest.

The peptides may also be produced by enzymatic or chemical cleavage of the purified IL8 receptor or a polypeptide having the desired sequence. Such procedures are conventional and well-known in the art.

In one embodiment, the inhibitors of the present invention can be polyclonal and monoclonal antibodies that can be made in vitro or in vivo. Methods of making such antibodies are known in the art.

Polyclonal antibodies against these peptides are generated by immunizing a suitable animal, such as a mouse, rat, rabbit, sheep or goat, with the peptide of interest. In order to enhance immunogenicity, the peptide can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the peptide may be conjugated to a bacterial toxoid, such as toxoid from diphtheria, tetanus, cholera, etc., in order to enhance the immunogenicity thereof.

Rabbits, sheep and goats are preferred for the preparation of polyclonal sera when large volumes of sera are desired. These animals are good design choices also because of the availability of labeled anti-rabbit, anti-sheep and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). The animal is generally boosted 2–6 weeks later with one or more injections of the protein in saline, preferably using Freund's incomplete adjuvant. Antibodies may also be generated by in vitro immunization, using methods known in the art. Polyclonal antisera is then obtained from the immunized animal.

Monoclonal antibodies are generally prepared using the method of Kohler and Milstein, *Nature* (1975) 256:495–96, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the protein antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (as ascites in mice).

Functional fragments of the antibody inhibitors will also find use with the present invention and can be produced by cleaving a constant region, not responsible for antigen binding, from the antibody molecule, using e.g., pepsin, to produce F(ab')$_2$ fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques. These fragments are known as $F_v$.

Chimeric or humanized antibodies can also be produced for use in the present invention. These antibodies can be designed to minimize unwanted immunological reactions attributable to heterologous constant and species-specific framework variable regions typically present in monoclonal and polyclonal antibodies. For example, if the antibodies are to be used as IL8 inhibitors in human subjects, chimeric antibodies can be created by replacing non-human constant regions, in either the heavy and light chains, or both, with human constant regions, using techniques generally known in the art. See, e.g., Winter, G. and Milstein, C. (1991) *Nature* 349:293–299; Jones, P. T. et al. (1986) *Nature* 321:522–525; Riechmann, L. et al. (1988) 332:323–27; and Carter, P. et al. (1992) *Proc. Natl. Acad. Sci. USA* 89:4285–4289.

Also contemplated by the present invention are small molecule and peptide inhibitors which interact with the amino-terminal extracellular domain of the IL8 receptor and which compete with IL8 for binding to the receptor. For example, peptide libraries can be constructed and screened for peptides having the ability to bind with the IL8 receptor and inhibit IL8 binding thereto (see e.g., Zuckermann et al. *J. Mol. Biol.* (1992) 227:711–718 for a description of the production of peptide libraries.) Similarly, peptides, peptide mixtures and peptoids can be synthesized or generated by biological means and tested for their ability to inhibit IL8 binding to the receptor (see, e.g., Zuckermann et al. *Proc. Natl. Acad. Sci. USA* (1992) 89:4505–4509; Simon et al. *Proc. Natl. Acad. Sci. USA* (1992) 89:9367–9371; Cwirla, S. E. et al., *Proc. Natl. Acad. Sci. USA* (1990) 87:6378–6382; Devlin, J. J. et al., *Science* (1990) 249:404–406. Small molecules (i.e., potential mimetics), synthesized or derived from natural sources, can also be screened for the ability to inhibit IL8 binding to the receptor. Strategies for designing and identifying such mimetics are well known in the art. See, e.g., Fauchere, J. L. in *Advances in Drug Research*, Vol. 15, p.28–69 (1986); Morgan et al. *Ann. Rep. Med. Chem.* (1989) 24:243–252; Hruby et al. *Biochem. J.* (1990) 268:249–262.

The above preparations can be tested for their ability to bind the IL8 receptor and modulate IL8 receptor-mediated activity, using known assays. The substances can be tested for their ability to compete with IL8 for receptor binding using competition assays, such as the radioimmunoassays described in Gayle et al., *J. Biol. Chem.* (1993) 268:7283–7289; and LaRosa et al., *J. Biol. Chem.* (1992) 267:25402–25406 and in the examples herein. Compounds which compete with IL8 can be shown to interact with the receptor by methods outlined above. The ability of these molecules to interact with the amino-terminal extracellular domain of the receptor can be demonstrated, also by methods described above, using, for example, chimeric receptors shown to bind IL8, consisting of an amino-terminal extracellular domain of an IL8 receptor and another, unrelated, receptor.

Furthermore, the ability of the inhibitors to modulate IL8 receptor-mediated activity can be tested, as explained above, by the measurement of e.g., free cytosolic $Ca^2+$levels, intracellular $IP_3$ concentrations and DAG levels (see, e.g., International Publication No. WO93/06229 (published Apr. 1, 1993); Bazzoni, F. et al. (1991) *J. Exp. Med.* 173:771–774; Peveri, P. et al. (1988) *J. Exp. Med.* 167:1547–1559). Other measurements of IL8 mediated activity include neutrophil chemotaxic assays (see, e.g., Schröder, J. M. et al. (1987) *J. Immunol.* 139:3474–3483; Fincham, N. J. et al. (1988) *J. Immunol.* 140:4294–4299; Larson, C. G. et al. (1989) *Science* 243:1464–1466; Grob, P. M. et al. (1990) *J. Biol. Chem.* 265:8311–8316; Strieter, R. M. et al. (1989) *J. Biol. Chem.* 264:10621–10626); enzyme release assays, such as PMN peroxidase-releasing activity assays, β-glucoronidase release assays, $O_2$-release as determined by cytochrome C assays and elastase release assays (see, e.g., Schröder, J. M. et al. (1987) *J. Immunol.* 139:3474–3483; Peveri, P. et al. (1988) *J. Exp. Med.* 167:1547–1559).

Antibody inhibitors of the present invention are not only useful as modulators of IL8 activity, but may be used to identify homologous IL8 receptor genes in other vertebrate species and to immunopurify the IL8 receptor from sources producing the same. Finally, the antibodies can also be used as targeting agents to deliver other IL8 agonists and antagonists to IL8 binding sites. In order to do so, the antibodies can be conjugated to these agents or fusion proteins, including at least the active binding region of the antibody linked to a least a functionally active portion of an IL8 inhibitor, can be constructed using recombinant DNA techniques well known in the art.

The inhibitors of the present invention can be provided in pharmaceutical compositions for inhibiting IL8 binding to its receptor and modulating an IL8 receptor-mediated biological response. The compositions will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

Pharmaceutical compositions comprise an effective inhibiting or modulating amount of an IL8 inhibitor, as defined above. The compositions are conventionally administered parenterally, e.g., by injection, either intravenously, subcutaneously, intramuscularly or intraperitonealy. Additional formulations suitable for other modes of administration include oral and pulmonary formulations, suppositories, and transdermal applications. Dosage treatment may be a single dose schedule or a multiple dose schedule.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Peptide and Antisera Preparation

Peptide synthesis, conjugation to toxoids, immunization of mice and sheep and determination of ELISA reactivity against pin-coupled and plate-coated peptide were performed by Chiron Mimotopes Pty. Ltd. (Clayton, Victoria 3168, Australia) employing standard procedures. In particular, peptides having substantial homology to portions of the amino-terminal extracellular region of human IL8 receptors IL8R1 and IL8R2, as shown in Tables 1 and 2, were synthesized using standard techniques. Some of the peptides (as indicated in the Tables) were coupled via an internal cysteine residue to a toxin to increase the immunogenicity thereof. The N-terminal acetyl or C-terminal β-alanine-diketopeperazine groups are blocking groups to mimic the environment of the peptide sequence within the protein.

Antisera were raised in mice against peptides #1 and #3 and in sheep against peptide #1 (FIG. 1, Table 1). Antisera to the IL8R2 amino-terminal extracellular domain were raised in mice against peptides #6 and #7 and in sheep against a mixture of peptides, #10, #11, #12, #13 (FIG. 1, Table 2). Immune sera, but not preimmune sera nor antisera against peptides #6 and #7, showed high titer against the immunizing peptide(s) as determined by ELISA against the peptide on pins and/or coated on plates. Technical difficulties were cited by the manufacturer as the explanation for lack of immunoactivity of antisera against immunizing peptides #6 and #7. These particular antisera were not pursued and antisera against peptides #10–13 were used instead.

Antisera were either used untreated, or were purified either by chromatography on Protein G Agarose (Pharmacia) or by affinity chromatography on peptide #1 Sepharose (for anti IL8R1 immune sera) or peptide #10

Sepharose (for anti-IL8R2 immune sera). Peptides conjugated to Sepharose were prepared by Chiron Mimotopes.

TABLE 1

Peptides from the Amino-terminal Extracellular Domain of IL8-R1

| Peptide | | |
|---|---|---|
| * 1 | amino-MSNITDPQMWDFDDLXC-dkp | (SEQ ID NO:6) |
| 1b | amino-MSNITDPQMWDFDDLXG-amide | (SEQ ID NO:7) |
| 1c | amino-MSNITDPQMWDFDDLXC-dkp-thiopropylsepharose | (SEQ ID NO:8) |
| * 3 | acetyl-NFTGMPPADEDYSPXC-dkP | (SEQ ID NO:9) |
| 3b | acetyl-NFTGMPPADEDYSPXG-amide | (SEQ ID NO:10) |

*= antisera produced
X= β-alanine
dkp= diketopiperazine

TABLE 2

Peptides from the Amino-terminal Extracellular Domain of IL8-R2

| Peptide | | |
|---|---|---|
| * 6 | amino-MESDSFEDFWKGEDLSNYSYXCX-dkp | (SEQ ID NO:11) |
| * 7 | acetyl-SSTLPPFLLDAAPCEPESLEIX-dkp | (SEQ ID NO:12) |
| 8 | amino-MESDSFEDFWKGEDLSNYSY-amide | (SEQ ID NO:13) |
| 9 | acetyl-SSTLPPFLLDAAPAEPESLEI-amide | (SEQ ID NO:14) |
| * 10 | amino-MESDSFEDFWKGEDLCX-dkp | (SEQ ID NO:15) |
| 10b | amino-MESDSFEDFWKGEDL-amide | (SEQ ID NO:16) |
| 10c | amino-MESDSFEDFWKGEDL-dkp-thiopropylsepharose | (SEQ ID NO:17) |
| * 11 | acetyl-FEDFWKGEDLSNYSYCX-dkp | (SEQ ID NO:18) |
| 11b | acetyl-FEDFWKGEDLSNYSY-amide | (SEQ ID NO:19) |
| * 12 | acetyl-SSTLPPFLLDAAPCX-dkp | (SEQ ID NO:20) |
| 12b | acetyl-SSTLPPFLLDAAPA-amide | (SEQ ID NO:21) |
| * 13 | acetyl-FLLDAAPCEPESLEIX-dkp | (SEQ ID NO:22) |
| 13b | acetyl-FLLDAAPAEPESLEI-amide | (SEQ ID NO:23) |

*= antisera produced
X= β-alanine
dkp= diketopiperazine

EXAMPLE II

Neutrophil IL8 Receptor Recognition Assays

Antibodies were tested for their ability to recognize neutrophils as follows. Neutrophils were isolated from whole blood using Neutrophil Isolation Media (NIM) (Cardinal) essentially as described by the manufacturer with the following modifications. 20 ml NIM and 30 ml blood in 50 ml tubes were centrifuged for 50 minutes. Contaminating red blood cells were removed by lysis in ice cold water. The resulting neutrophils were resuspended in Hank's Buffered Saline (HBS) and stored on ice.

Neutrophils were incubated and subjected to FACS analysis as follows. Neutrophils were stained for FACS analysis by resuspending $1 \times 10^6$ cells in 50 µl of sheep pre-immune IgG (FIGS. 2A and 2C), anti-IL8R1 peptide IgG (FIG. 2B) or anti-IL8R2 peptide IgG (FIG. 2D), each diluted 1:150 in PBS+1% BSA. Cells were incubated 2 hours on ice, centrifuged at 1000 RPM for 5 minutes and then washed twice with PBS+1% BSA. Washed cells were resuspended in 50 µl FITC-conjugated F(ab')$_2$ fragment rabbit anti-sheep IgG (H+L) antibody (1:100 in PBS+1% BSA, Jackson ImmunoResearch Laboratories). Cells were incubated 1 hour on ice, centrifuged at 1000 RPM for 5 minutes, washed in PBS+1% BSA and then washed in PBS. Cells to be analyzed immediately were suspended in 500 ml of PBS. Propidium iodide was added at 2.5 ng/ml as a viability stain. Neutrophils could be fixed in 1% paraformaldehyde and analyzed up to 72 hours later. Labelled cells were analyzed on a FACSCAN (Becton Dickonson).

As can be seen in FIG. 2, antisera to the amino-terminal extracellular domain IL8R1 peptide #1 (FIG. 2B) or IL8R2 peptides #10–13 (FIG. 2D), but not preimmune sera (FIGS. 2A and 2C), recognized neutrophils. This indicates that antisera raised against peptide(s) from the amino-terminal extracellular domain of the IL8 receptors can recognize native receptor. Antiserum raised against IL8R1 peptide #3, though of high titer against the immunizing peptide, did not recognize neutrophils (data not shown). This result indicates nothing about the role of IL8R1 peptide #3 sequence in ligand recognition but means only that peptide #3 was not present in sufficient amounts in a receptor mimetic conformation to elicit anti-receptor antibodies as opposed to just anti-peptide antibodies. Antisera raised against either IL8R2 peptides #6 or #7 showed low titer against the immunizing peptides and were not continued.

Example III

Receptor Binding Assays

Antibodies were tested for their ability to block the binding of IL8 to its receptor as follows. IL8R1 and IL8R2, for use in the receptor binding assays, were produced recombinantly. DNA encoding IL8R1 and IL8R2 was isolated from human genomic DNA by PCR using oligonucleotide primers based on published sequences for IL8R1 (Holmes et al. *Science* (1991) 253:1278) and IL8R2 (Murphy and Tiffany, *Science* (1991) 253:1280). The nucleotide sequence of the isolated genes was confirmed by dideoxy sequencing.

The sequence encoding IL8R1 (in baculovirus transfer vector pVL1392, Invitrogen) or IL8R2 (in the pAcC13 transfer vector described in Munemitsu et al. *Mol. Cell. Biol.* (1990) 10:5977) was recombined into the Autographa California baculovirus (AcNPV) by co-transfecting 2 µg of recombinant receptor transfer vector with 0.5 ug of linearized wild-type viral DNA into Sf9 cells as described (Kitts et al. *Nuc. Acids. Res.* (1991) 18:5667). Recombinant baculovirus were isolated by plaque purification (Smith et al. *Mol. Cell. Biol.* (1983) 3:2156). Suspension cultures of ~$1.5 \times 10^6$ Sf9 cells per ml were harvested for analysis following 40–48 hours infection with the relevant baculovirus stock at MOI of 2–10, in serum free medium (Maiorella et al. *Biotech.* (1988) 6:1406).

Sf9 insect cells were infected with recombinant IL8R1 or IL8R2 baculovirus and seeded into 96-well Remova-wells culture plates in ExCell 400 media. At 40–48 hours post-infection, culture medium was removed and cell monolayers were pretreated for 1 hour at room temperature with antibody in Hepes-BSA binding buffer (25 mM Hepes, pH7.5, 150 mM NaCl, 5 mM CaCl$_2$, 5 mM MgCl$_2$, 1 mg/mL bovine serum albumin). $^{125}$I-IL8 was added to give 0.2 nM final concentration and incubation was continued at room temperature for 3 hour. Cells were washed once with Hepes-BSA binding buffer, and bound $^{125}$I-IL8 was determined by gamma counting. Non-specific binding was measured in the presence of 1 µg/ml unlabeled IL8. Data are the average of duplicate determinations.

Figure 3:
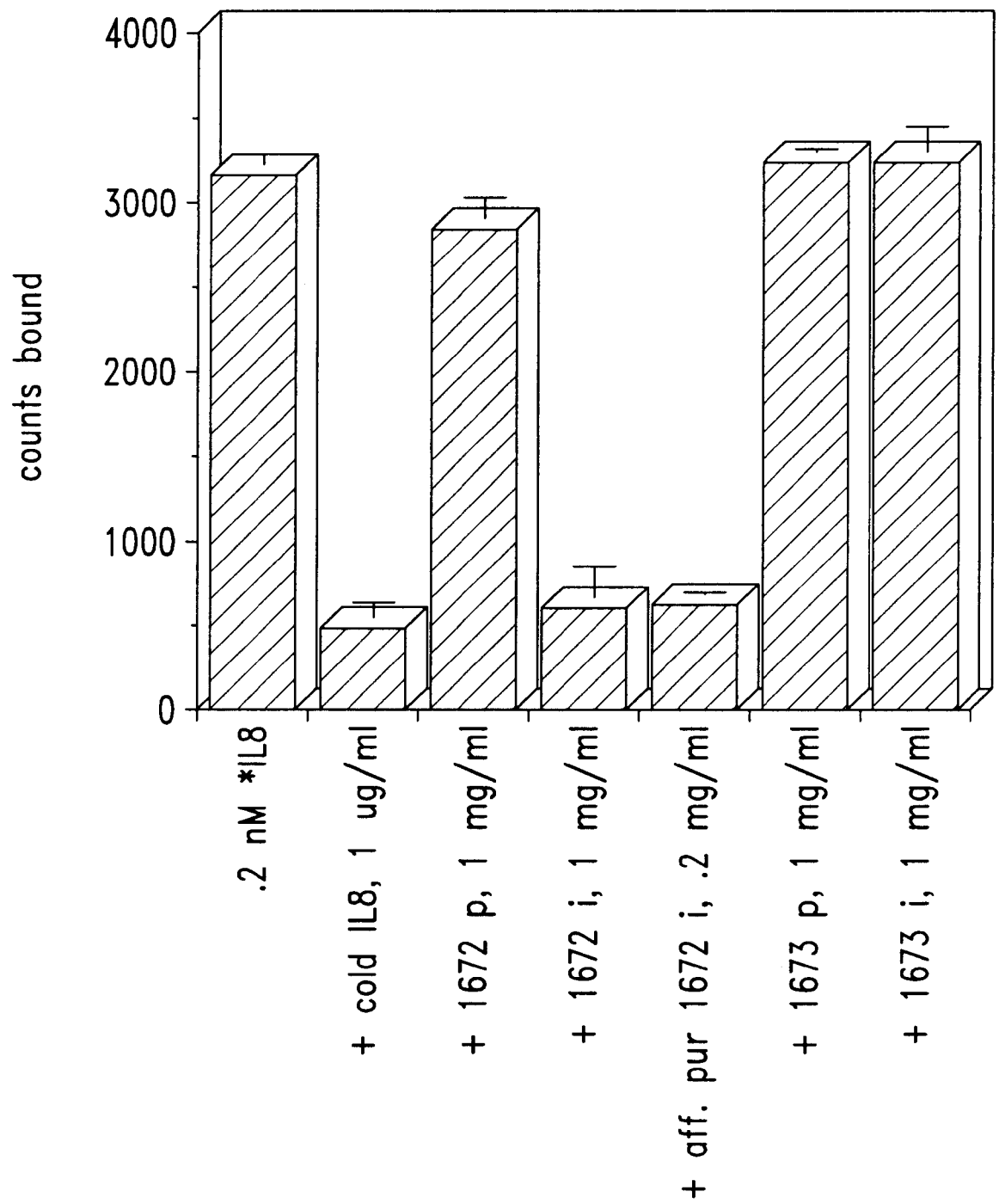
FIG. 3 depicts the results of receptor binding assays for IL8R1, as described in the examples. Sf9 cells were infected with recombinant baculovirus for expression of IL8R1 and binding of $^{125}$I-IL8 was assayed as described after a 1 hour preincubation with IL8 or antibodies: 1672 p, IgG fraction from preimmune serum control for IL8R1 peptide #1 serum; 1672 i, IgG fraction from antiserum to peptide #1; Aff pur 1672 i, affinity purified antibodies to IL8R1 peptide #1; 1673 p, IgG fraction from preimmune serum control for IL8R2 peptides #10–13 serum, 1673 i, IgG fraction from antiserum to IL8R2 peptides #10–13. The final concentrations of each effector are indicated.
Figure 5:
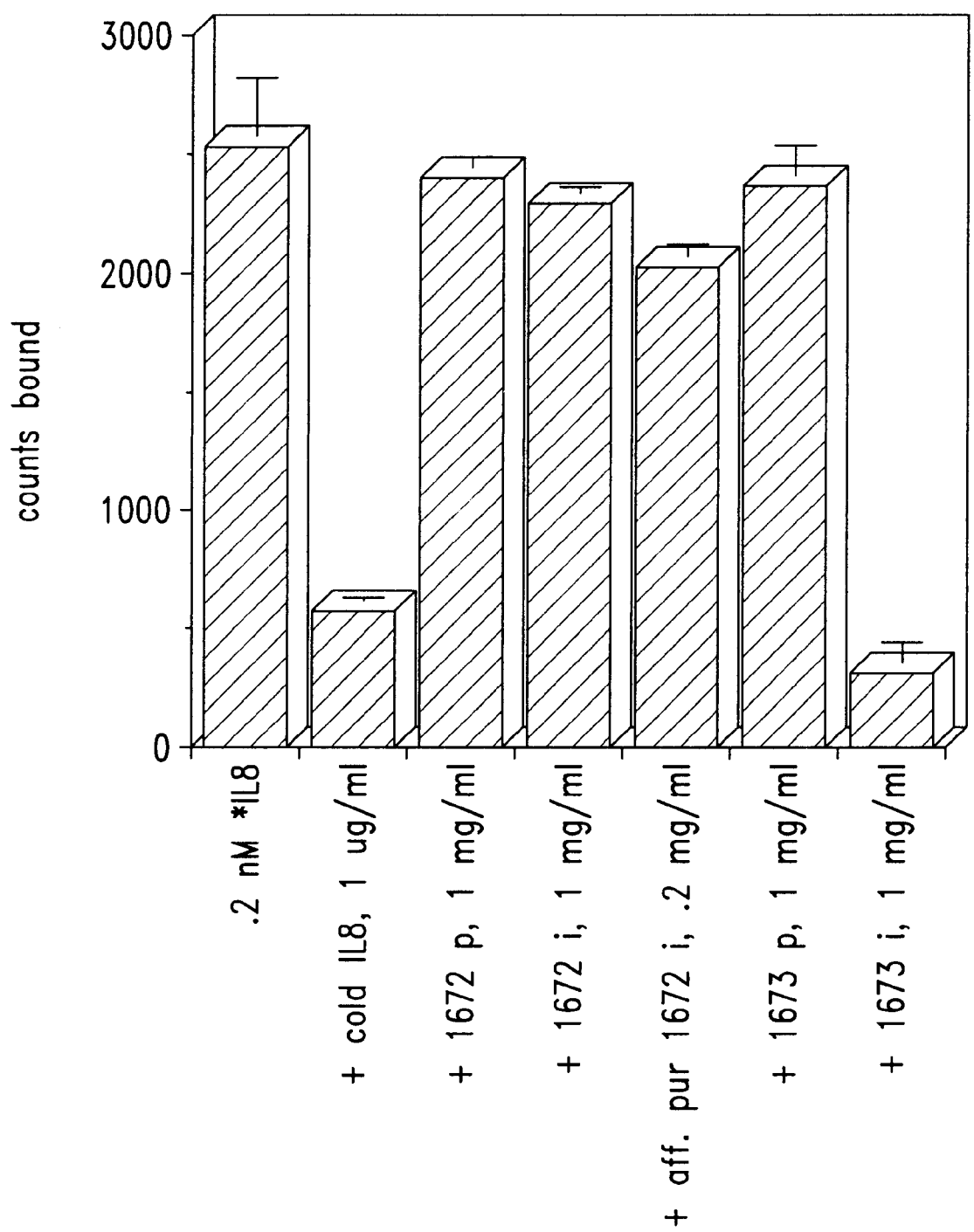
FIG. 5 depicts the results of receptor binding assays for IL8R2, as described above and in the examples.

Antiserum to IL8R1 peptide #1, but not preimmune antiserum, blocked binding of $^{125}$I-IL8 to IL8R1 receptors expressed on recombinant baculovirus-infected Sf9 cells (FIG. 3). Antiserum to IL8R1 peptide #1 did not inhibit binding of IL8 to IL8R2 (FIG. 5). Therefore this antiserum specifically neutralized IL8 binding to IL8R1. The epitope on the IL8R1 recognized by anti-IL8R1 peptide #1 antibodies is near to or overlapping the IL8 recognition site on IL8R1.

Figure 4:
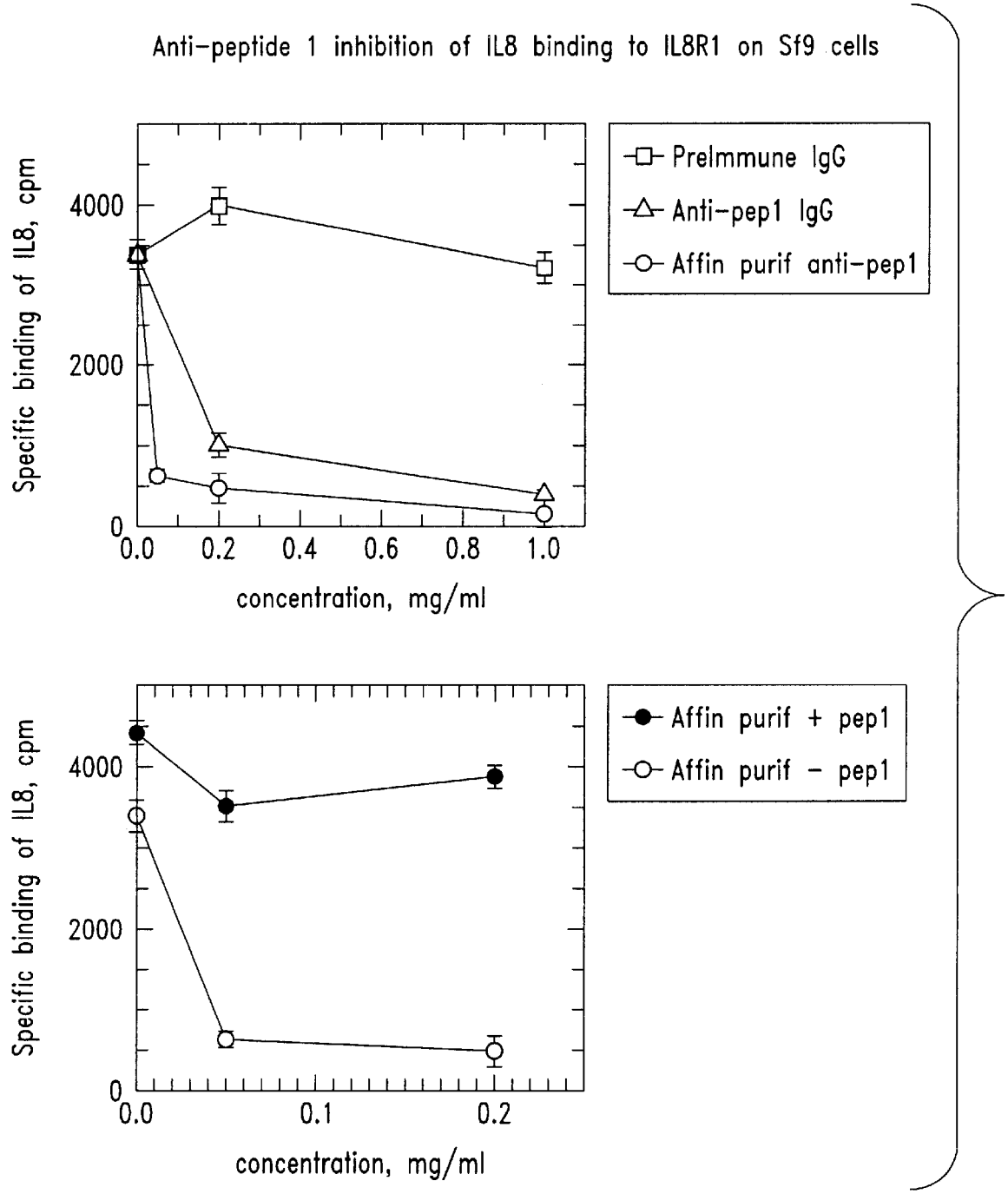
FIG. 4 shows anti-IL8R1 peptide #1 inhibition of IL8 binding to IL8R1 on Sf9 cells. Sf9 cells were infected with baculovirus for IL8R1, preincubated with antibodies, and assayed for $^{125}$I-IL8 binding as described above. Where indicated (Affin purif+pep1), the affinity purified antibodies to IL8R1 peptide #1 were pre-absorbed with 50 mg/mL of peptide #1 prior to use. Data are corrected for non-specific binding as measured in the presence of 1 mg/ml of unlabeled IL8.

The ability of anti IL8R1 peptide #1 antibodies to neutralize the binding of IL8 to its receptor was abrogated by excess IL8R1 peptide #1, confirming the specificity of the antiserum (FIG. 4). Thus epitope(s) for the neutralization of IL8 binding are contained within the corresponding region of the IL8R1, amino-terminal extracellular domain amino acid residues 1–15. These results suggest that the IL8R1 amino-terminal extracellular domain is involved in IL8 recognition.

Antiserum to IL8R2 peptide pool #10–13, but not preimmune antiserum, blocked binding of $^{125}$I-IL8 to IL8R2 receptors expressed on recombinant baculovirus-infected Sf9 cells (FIG. 5). Antiserum to IL8R2 peptides #10–13 did not inhibit IL8 binding to IL8R1 (FIG. 3). Therefore this antiserum specifically neutralized IL8 binding to IL8R2 and recognized epitope(s) near to, or overlapping with, the IL8 recognition sequence of IL8R2.

Figure 6:
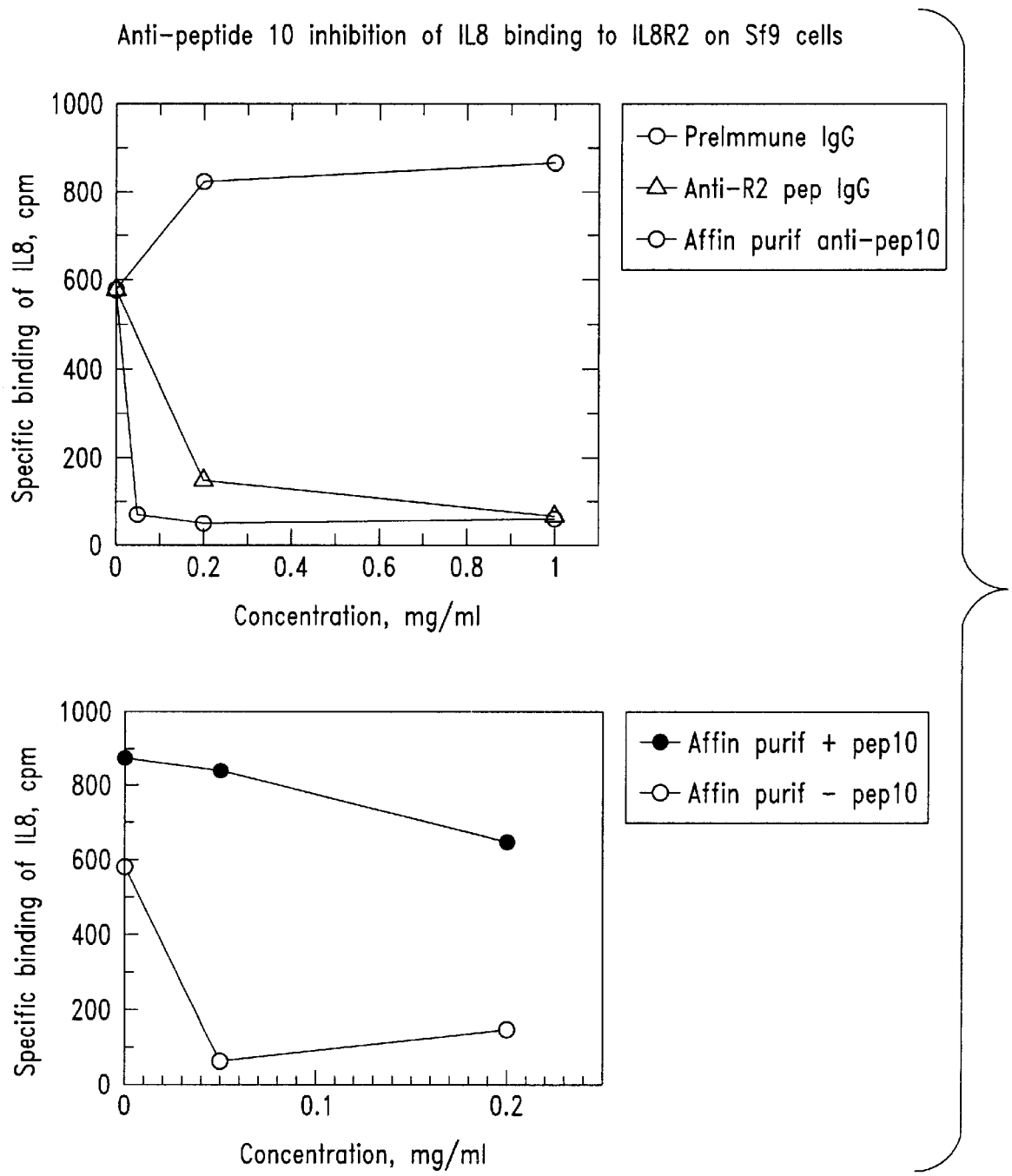
FIG. 6 shows anti-IL8R2 peptide #10 inhibition of IL8 binding to IL8R2 on Sf9 cells. Sf9 cells were infected with baculovirus for IL8R2, preincubated with antibodies, and assayed for $^{125}$I-IL8 binding as described above. Antibody additions are as follows: PreImmune IgG, IgG fraction from preimmune serum control; Anti-R2 pep IgG, IgG fraction from antiserum to IL8R2 peptides#10–13; Affin purif anti-pep10 or Affin purif–pep10, affinity purified antibodies to peptide #10; Affin purif+pep10, affinity purified antibody to peptide #10 pre-absorbed with 50 mg/ml of peptide #10. Data are corrected for non-specific binding as measured in the presence of 1 mg/ml unlabeled IL8.

Antiserum to peptides #10–13 was fractionated by peptide #10 affinity chromatography. Antibodies to IL8R2 peptide #10 inhibited IL8 binding to IL8R2 receptors expressed on Sf9 cells (FIG. 6). Free peptide #10 blocked neutralization by this antibody and confirmed that peptide #10 includes epitope(s) at or near to the IL8 recognition site on IL8R2 (FIG. 6). This corresponds to a neutralizing epitope(s) within the region of amino acid residues 1–15 of the IL8R2. Depletion of anti-peptide #10 antibodies did not abolish the ability of the anti-IL8R2 peptide antiserum to inhibit IL8 binding to IL8R2 (data not shown). This indicates that there are additional epitope(s) within the remainder of the amino-terminal extracellular region of IL8R2, amino acid residues 16–41, that also contribute to the neutralizing activity of the anti-IL8R2 peptide antiserum. These results suggest that amino acids 1–41 in the amino-terminal extracellular domain of IL8R2 include sequences involved in the recognition of IL8.

Thus, novel IL8 inhibitors, as well as methods for using the same, are disclosed. Although preferred embodiments of the subject invention have been described in some detail, it is understood that obvious variations can be made without departing from the spirit and the scope of the invention as defined by the appended claims.

What is claimed is:

1. An isolated inhibitor of IL8 receptor 2-binding wherein said inhibitor is an antibody capable of
   (a) competing with IL8 for binding to the IL8 receptor 2; and
   (b) interacting with residues of a peptide of the amino-terminal extracellular domain of the IL8 receptor 2 wherein the peptide comprises the sequence M-E-S-D-S-F-E-D-F-W-K-G-E-D-L (SEQ ID NO:2).

2. The inhibitor according to claim 1, wherein the antibody is obtainable by immunizing a mammal with an immunogen that comprises a polypeptide comprising the amino acid sequence M-E-S-D-S-F-E-D-F-W-K-G-E-D-L (SEQ ID NO:2).

3. An isolated inhibitor of IL8 receptor 2-binding wherein said inhibitor is an antibody capable of
   (a) competing with IL8 for binding to the IL8 receptor 2; and
   (b) interacting with the amino terminal extracellular domain of the IL8 receptor 2, wherein the antibody is obtainable by immunizing a mammal with an immunogen and wherein the immunogen comprises at least four polypeptides, wherein (i) the amino acid sequence of the first polypeptide comprises the amino acid sequence M-E-S-D-S-F-E-D-F-W-K-G-E-D-L (SEQ ID NO:2);
(ii) the amino acid sequence of the second polypeptide comprises the amino acid sequence F-E-D-F-W-K-G-E-D-L-S-N-Y-S-Y (SEQ ID NO:3);
(iii) the amino acid sequence of the third polypeptide comprises the amino acid sequence S-S-T-L-P-P-F-L-L-D-A-A-P-C (SEQ ID NO:4); and
(iv) the amino acid sequence of the fourth polypeptide comprises the amino acid sequence F-L-L-D-A-A-P-C-E-P-E-S-L-E-I (SEQ ID NO:5).

4. An isolated inhibitor IL8 receptor 2-binding wherein said inhibitor is an antibody capable of (a) competing with IL8 for binding to the IL8 receptor 2;
(b) interacting with residues of a peptide of the amino-terminal extracellular domain of the IL8 receptor 2, and
(c) is obtainable by immunizing a mammal with an immunogen comprises at least three polypeptides, wherein
  (i) the amino acid sequence of the first polypeptide comprises the amino acid sequence F-E-D-F-W-K-G-E-D-L-S-N-Y-S-Y (SEQ ID NO:3);
  (ii) the amino acid sequence of the second polypeptide comprises the amino acid sequence S-S-T-L-P-P-F-L-L-D-A-A-P-C (SEQ ID NO:4); and
  (iii) the amino acid sequence of the third polypeptide comprises the amino acid sequence F-L-L-D-A-A-P-C-E-P-E-S-L-E-I (SEQ ID NO:5).

* * * * *

```
                            SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Met Ser Asn Ile Thr Asp Pro Gln Met Trp Asp Phe Asp Asp Leu
1               5                   10                  15

(2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Met Glu Ser Asp Ser Phe Glu Asp Phe Trp Lys Gly Glu Asp Leu
1               5                   10                  15

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Phe Glu Asp Phe Trp Lys Gly Glu Asp Leu Ser Asn Tyr Ser Tyr
1               5                   10                  15

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ser Ser Thr Leu Pro Pro Phe Leu Leu Asp Ala Ala Pro Cys
1               5                   10

(2) INFORMATION FOR SEQ ID NO:5:
```

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:5:

```
Phe Leu Leu Asp Ala Ala Pro Cys Glu Pro Glu Ser Leu Glu Ile
1               5                  10                  15
```

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an amino."

(ix) FEATURE:
        (A) NAME/KEY: Modified-site
        (B) LOCATION: 16
        (D) OTHER INFORMATION: /note= "The amino acid is a
            beta-alanine."

(ix) FEATURE:
        (A) NAME/KEY: Modified-site
        (B) LOCATION: 17
        (D) OTHER INFORMATION: /note= "The terminal amino acid
            includes a diketopiperize."

(xi) SEQUENCE DESCRIPTION: SEQ ID NO:6:

```
Met Ser Asn Ile Thr Asp Pro Gln Met Trp Asp Phe Asp Asp Leu Xaa
1               5                  10                  15

Cys
```

(2) INFORMATION FOR SEQ ID NO:7:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an amino."

(ix) FEATURE:
        (A) NAME/KEY: Modified-site
        (B) LOCATION: 16
        (D) OTHER INFORMATION: /note= "The amino acid is a
            beta-alanine."

(ix) FEATURE:
        (A) NAME/KEY: Modified-site
        (B) LOCATION: 17
        (D) OTHER INFORMATION: /note= "The terminal amino acid
            includes an amide."

(xi) SEQUENCE DESCRIPTION: SEQ ID NO:7:

```
Met Ser Asn Ile Thr Asp Pro Gln Met Trp Asp Phe Asp Asp Leu Xaa
1               5                   10                  15
Gly
```

(2) INFORMATION FOR SEQ ID NO:8:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an amino."

(ix) FEATURE:
        (A) NAME/KEY: Modified-site
        (B) LOCATION: 16
        (D) OTHER INFORMATION: /note= "The amino acid is a
            beta-alanine."

(ix) FEATURE:
        (A) NAME/KEY: Modified-site
        (B) LOCATION: 17
        (D) OTHER INFORMATION: /note= "The terminal amino acid
            includes a diketopiperize and a thiopropylsepharose."

(xi) SEQUENCE DESCRIPTION: SEQ ID NO:8:

```
Met Ser Asn Ile Thr Asp Pro Gln Met Trp Asp Phe Asp Asp Leu Xaa
1               5                   10                  15
Cys
```

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an acetyl."

(ix) FEATURE:
        (A) NAME/KEY: Modified-site
        (B) LOCATION: 15
        (D) OTHER INFORMATION: /note= "The amino acid is a
            beta-alanine."

(ix) FEATURE:
        (A) NAME/KEY: Modified-site
        (B) LOCATION: 16
        (D) OTHER INFORMATION: /note= "The terminal amino acid
            includes a diketopiperize."

(xi) SEQUENCE DESCRIPTION: SEQ ID NO:9:

```
Asn Phe Thr Gly Met Pro Pro Ala Asp Glu Asp Tyr Ser Pro Xaa Cys
1               5                   10                  15
```

(2) INFORMATION FOR SEQ ID NO:10:

```
    (i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an acetyl."

(ix) FEATURE:
        (A) NAME/KEY: Modified-site
        (B) LOCATION: 15
        (D) OTHER INFORMATION: /note= "The amino acid is a
            beta-alanine."

(ix) FEATURE:
        (A) NAME/KEY: Modified-site
        (B) LOCATION: 16
        (D) OTHER INFORMATION: /note= "The terminal amino acid
            includes a diketopiperize."

(xi) SEQUENCE DESCRIPTION: SEQ ID NO:10:

Asn Phe Thr Gly Met Pro Pro Ala Asp Glu Asp Tyr Ser Pro Xaa Gly
1               5                  10                  15

(2) INFORMATION FOR SEQ ID NO:11:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an amino."

(ix) FEATURE:
        (A) NAME/KEY: Modified-site
        (B) LOCATION: 21
        (D) OTHER INFORMATION: /note= "The amino acid is a
            beta-alanine."

(ix) FEATURE:
        (A) NAME/KEY: Modified-site
        (B) LOCATION: 23
        (D) OTHER INFORMATION: /note= "The terminal amino acid
            is a beta-alanine and includes a diketopiperize."

(xi) SEQUENCE DESCRIPTION: SEQ ID NO:11:

Met Glu Ser Asp Ser Phe Glu Asp Phe Trp Lys Gly Glu Asp Leu Ser
1               5                  10                  15

Asn Tyr Ser Tyr Xaa Cys Xaa
                20

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide
```

```
    (ix) FEATURE:
         (A) NAME/KEY: Modified-site
         (B) LOCATION: 1
         (D) OTHER INFORMATION: /note= "The terminal position
             includes an acetyl."

(ix) FEATURE:
         (A) NAME/KEY: Modified-site
         (B) LOCATION: 16
         (D) OTHER INFORMATION: /note= "The terminal amino acid
             is a beta-alanine and includes diketopiperazine."

(xi) SEQUENCE DESCRIPTION: SEQ ID NO:12:

Ser Ser Thr Leu Pro Pro Phe Leu Leu Asp Ala Ala Pro Cys Glu Pro
1               5                  10                  15

(2) INFORMATION FOR SEQ ID NO:13:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "The terminal position
             includes an amino."

(ix) FEATURE:
         (A) NAME/KEY: Modified-site
         (B) LOCATION: 20
         (D) OTHER INFORMATION: /note= "The terminal amino acid
             includes an amide."

(xi) SEQUENCE DESCRIPTION: SEQ ID NO:13:

Met Glu Ser Asp Ser Phe Glu Asp Phe Trp Lys Gly Glu Asp Leu Ser
1               5                  10                  15

Asn Tyr Ser Tyr
            20

(2) INFORMATION FOR SEQ ID NO:14:

(i) SEQUENCE CHARACTERISTICS:
         (A) LENGTH: 21 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "The terminal position
             includes an acetyl."

(ix) FEATURE:
         (A) NAME/KEY: Modified-site
         (B) LOCATION: 21
         (D) OTHER INFORMATION: /note= "The terminal amino acid
             includes an amide."

(xi) SEQUENCE DESCRIPTION: SEQ ID NO:14:

Ser Ser Thr Leu Pro Pro Phe Leu Leu Asp Ala Ala Pro Ala Glu Pro
1               5                  10                  15

Glu Ser Leu Glu Ile
            20
```

(2) INFORMATION FOR SEQ ID NO:15:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an amino."

(ix) FEATURE:
        (A) NAME/KEY: Modified-site
        (B) LOCATION: 17
        (D) OTHER INFORMATION: /note= "The terminal amino acid
            is a beta-alanine and includes a diketopiperazine."

(xi) SEQUENCE DESCRIPTION: SEQ ID NO:15:

```
Met Glu Ser Asp Ser Phe Glu Asp Phe Trp Lys Gly Glu Asp Leu Cys
1               5                   10                  15

Xaa
```

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an amino."

(ix) FEATURE:
        (A) NAME/KEY: Modified-site
        (B) LOCATION: 15
        (D) OTHER INFORMATION: /note= "The terminal amino acid
            includes an amide."

(xi) SEQUENCE DESCRIPTION: SEQ ID NO:16:

```
Met Glu Ser Asp Ser Phe Glu Asp Phe Trp Lys Gly Glu Asp Leu
1               5                   10                  15
```

(2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an amino."

(ix) FEATURE:
        (A) NAME/KEY: Modified-site
        (B) LOCATION: 15
        (D) OTHER INFORMATION: /note= "The terminal amino acid includes a diketopiperazine and thiopropylsepharose."

(xi) SEQUENCE DESCRIPTION: SEQ ID NO:17:

Met Glu Ser Asp Ser Phe Glu Asp Phe Trp Lys Gly Glu Asp Leu
1               5                   10                  15

(2) INFORMATION FOR SEQ ID NO:18:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an acetyl."

(ix) FEATURE:
        (A) NAME/KEY: Modified-site
        (B) LOCATION: 17
        (D) OTHER INFORMATION: /note= "The terminal amino acid
            is a beta-alanine and includes a diketopiperazine."

(xi) SEQUENCE DESCRIPTION: SEQ ID NO:18:

Phe Glu Asp Phe Trp Lys Gly Glu Asp Leu Ser Asn Tyr Ser Tyr Cys
1               5                   10                  15
Xaa (2) INFORMATION FOR SEQ ID NO:19:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an acetyl."

(ix) FEATURE:
        (A) NAME/KEY: Modified-site
        (B) LOCATION: 15
        (D) OTHER INFORMATION: /note= "The terminal amino acid
            includes an amide."

(xi) SEQUENCE DESCRIPTION: SEQ ID NO:19:

Phe Glu Asp Phe Trp Lys Gly Glu Asp Leu Ser Asn Tyr Ser Tyr
1               5                   10                  15

(2) INFORMATION FOR SEQ ID NO:20:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1

(D) OTHER INFORMATION: /note= "The terminal position
            includes an acetyl."

(ix) FEATURE:
        (A) NAME/KEY: Modified-site
        (B) LOCATION: 15
        (D) OTHER INFORMATION: /note= "The terminal amino acid
            is a beta-alanine and includes a diketopiperazine."

(xi) SEQUENCE DESCRIPTION: SEQ ID NO:20:

Ser Ser Thr Leu Pro Pro Phe Leu Leu Asp Ala Ala Pro Cys Xaa
1               5                   10                  15

(2) INFORMATION FOR SEQ ID NO:21:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an acetyl."

(ix) FEATURE:
        (A) NAME/KEY: Modified-site
        (B) LOCATION: 14
        (D) OTHER INFORMATION: /note= "The terminal amino acid
            includes an amide."

(xi) SEQUENCE DESCRIPTION: SEQ ID NO:21:

Ser Ser Thr Leu Pro Pro Phe Leu Leu Asp Ala Ala Pro Ala
1               5                   10

(2) INFORMATION FOR SEQ ID NO:22:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "The terminal position
            includes an acetyl."

(ix) FEATURE:
        (A) NAME/KEY: Modified-site
        (B) LOCATION: 16
        (D) OTHER INFORMATION: /note= "The terminal amino acid
            is a beta-alanine and includes a diketopiperazine."

(xi) SEQUENCE DESCRIPTION: SEQ ID NO:22:

Phe Leu Leu Asp Ala Ala Pro Cys Glu Pro Glu Ser Leu Glu Ile Xaa
1               5                   10                  15

(2) INFORMATION FOR SEQ ID NO:23:

(i) SEQUENCE CHARACTERISTICS:
        (A) LENGTH: 15 amino acids
        (B) TYPE: amino acid
        (C) STRANDEDNESS: single
        (D) TOPOLOGY: linear

```
        (ii) MOLECULE TYPE: peptide (ix) FEATURE:
             (A) NAME/KEY: Modified-site
             (B) LOCATION: 1
             (D) OTHER INFORMATION: /note= "The terminal position
                 includes an acetyl."

(ix) FEATURE:
             (A) NAME/KEY: Modified-site
             (B) LOCATION: 15
             (D) OTHER INFORMATION: /note= "The terminal amino acid
                 includes an amide."

(xi) SEQUENCE DESCRIPTION: SEQ ID NO:23:

Phe Leu Leu Asp Ala Ala Pro Ala Glu Pro Glu Ser Leu Glu Ile
1               5                   10                  15

(2) INFORMATION FOR SEQ ID NO:24:

(i) SEQUENCE CHARACTERISTICS:
             (A) LENGTH: 39 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:24:

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
                20                  25                  30

Glu Thr Glu Thr Leu Asn Lys
            35

(2) INFORMATION FOR SEQ ID NO:25:

(i) SEQUENCE CHARACTERISTICS:
             (A) LENGTH: 43 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:25:

Met Glu Ser Asp Ser Phe Glu Asp Phe Trp Lys Gly Glu Asp Leu Ser
1               5                   10                  15

Asn Tyr Ser Tyr Ser Ser Thr Leu Pro Pro Phe Leu Leu Asp Ala Ala
                20                  25                  30

Pro Cys Glu Pro Glu Ser Leu Glu Ile Asn Lys
            35                  40
```